United States Patent [19]

Boersma et al.

[11] 4,331,774

[45] May 25, 1982

[54] PROCESS FOR THE PREPARATION OF HYDROCARBONS

[75] Inventors: Michael A. M. Boersma; Martin F. M. Post; Lambert Schaper, all of Amsterdam, Netherlands

[73] Assignee: Shell Oil Company, Houston, Tex.

[21] Appl. No.: 169,550

[22] Filed: Jul. 17, 1980

[30] Foreign Application Priority Data

Jul. 20, 1979 [NL] Netherlands .................. 7905643

[51] Int. Cl.³ ............................................. C07C 1/04
[52] U.S. Cl. .................................... 518/714; 518/728; 585/408; 585/469; 252/455 R
[58] Field of Search ................ 585/408, 475, 469; 518/714, 728

[56] References Cited

U.S. PATENT DOCUMENTS

| | | | |
|---|---|---|---|
| 1,728,732 | 9/1929 | Jaeger | 585/475 X |
| 4,138,442 | 2/1979 | Chong et al. | 585/408 X |
| 4,213,921 | 7/1980 | Mitchell et al. | 568/909 X |
| 4,238,318 | 12/1980 | Kouwenhoven et al. | 585/408 X |

*Primary Examiner*—Bernard Helfin

[57] ABSTRACT

A process is disclosed for the preparation of aromatic hydrocarbon mixtures from a feed mixture of carbon monoxide and hydrogen by contacting said feed at elevated temperature and pressure with a mixture of two catalysts; one capable of converting said feed into acyclic oxygen containing hydrocarbons and the other certain crystalline gallium silicates.

9 Claims, No Drawings

PROCESS FOR THE PREPARATION OF HYDROCARBONS

BACKGROUND OF THE INVENTION

The invention relates to a process for the preparation of an aromatic hydrocarbon mixture from a mixture of carbon monoxide and hydrogen using a mixture of two catalysts of which one has the capability of catalyzing the conversion of an $H_2/CO$ mixture into acyclic oxygen-containing hydrocarbons, and the other is a crystalline silicate having the capability of catalyzing the conversion of acyclic oxygen-containing hydrocarbons into aromatic hydrocarbons. The crystalline silicates employed in the process to the invention are characterized in that they have the following properties:
(a) thermally stable up to a temperature above 600° C.,
(b) an X-ray powder diffraction pattern showing, inter alia, the reflections given in Table A.

TABLE A

| Radiation: Cu - K<br>2 θ | Wavelength 0.15418 nm<br>relative intensity |
| --- | --- |
| 7.8–8.2 | S |
| 8.7–9.1 | M |
| 11.8–12.1 | W |
| 12.4–12.7 | W |
| 14.6–14.9 | W |
| 15.4–15.7 | W |
| 15.8–16.1 | W |
| 17.6–17.9 | W |
| 19.2–19.5 | W |
| 20.2–20.6 | W |
| 20.7–21.1 | W |
| 23.1–23.4 | VS |
| 23.8–24.1 | VS |
| 24.2–24.8 | S |
| 29.7–30.1 | M | wherein the letters used have the following meanings:
VS=very strong; S=strong; M=moderate; W=weak; θ=angle according to Bragg.
(c) in the formula which gives the composition of the silicate, expressed in moles of the oxides, and in which, in addition to oxides of hydrogen, alkali metal and/or alkaline-earth metal and silicon, an oxide of a trivalent metal A are present, the $A_2O_3/SiO_2$ molar ratio (for the sake of brevity further designated m in this patent application) is less than 0.1.

In an investigation by the Applicants concerning the above-mentioned process using the catalyst mixtures in which as the crystalline silicate component an aluminum silicate has been employed, it has been found that the activity and selectivity of these catalyst mixtures are greatly dependent on m of the aluminum silicate. It has been found that catalyst mixtures in which an aluminum silicate with a low value for m is present, show a high selectivity and a low activity, whereas catalyst mixtures in which an aluminum silicate with a high value for m is present, show exactly the opposite behavior. For application of the process on a technical scale a catalyst mixture is needed which has both a high activity and a high selectivity.

Further investigation by the Applicants concerning the above-mentioned process has shown that this requirement can be met by using a crystalline silicate which has the properties mentioned under (a)-(c) and which contains as the trivalent metal gallium. For, with catalyst mixtures in which the crystalline aluminum silicate has been replaced by a crystalline gallium silicate, the catalytic behavior in the above-mentioned process has been found to be independent of m of the gallium silicate. Both with gallium silicates with a low value for m and with gallium silicates with a high value for m catalyst mixtures can be prepared which show, when using the above mentioned process, the high selectivity of a catalyst mixture which contains an aluminum silicate with a low value for m and, at the same time, the high activity of a catalyst mixture which contains an aluminum silicate with a high value for m.

SUMMARY OF THE INVENTION

The present patent application therefore relates to a process for the preparation of an aromatic hydrocarbon mixture, from a feed mixture of carbon monoxide and hydrogen which comprises contacting said feed in a contacting zone at an elevated temperature and pressure with a mixture of two catalysts of which one has the capability of catalyzing the conversion of an $H_2/CO$ mixture into acyclic oxygen-containing hydrocarbons and the other is a crystalline gallium silicate, having the following properties:
(a) thermally stable up to a temperature above 600° C.,
(b) an X-ray powder diffraction pattern showing, inter alia, the reflections given in Table A of the specification,
(c) in the formula which gives the composition of the silicate, expressed in moles of the oxides, and in which, in addition to oxides of hydrogen, alkali metal and/or alkaline-earth metal and silicon, gallium oxide is present, the $Ga_2O_3/SiO_2$ molar ratio (m) is less than 0.1, to produce a contact product, and separating an aromatic hydrocarbon mixture from said contact product.

DESCRIPTION OF PREFERRED EMBODIMENTS

In the process according to the invention the starting material is an $H_2/CO$ mixture. Such a mixture can very suitably be prepared by steam gasification of a carbon-containing material. Examples of such materials are brown coal, anthracite, coke, crude mineral oil and fractions thereof and oils produced from tar sand and bituminous shale. The steam gasification is preferably carried out at a temperature between 900° and 1500° C. and a pressure between 10 and 50 bar. In the process according to the invention the preferred starting material is an $H_2/CO$ mixture whose molar ratio lies between 0.25 and 1.0.

The process according to the invention is preferably carried out at a temperature in the range of about 200°–500° C. and particularly of 300°–450° C., a pressure of 1–150 bar and particularly of 5–100 bar and a space velocity of 50–5000 and particularly of 300–3000 Nl gas/l catalyst/h.

In the process according to the invention a mixture of two catalysts is used, which, for the sake of convenience, will be designated catalyst X and catalyst Y. Catalyst X is the one which is capable of catalyzing the conversion of an $H_2/CO$ mixture into acyclic oxygen-containing hydrocarbons and catalyst Y is the crystalline gallium silicate. Catalysts that are preferably used as X-catalysts are those which are capable of converting an $H_2/CO$ mixture into substantially methanol and/or dimethyl ether. Very suitable for the present purpose are catalysts which contain zinc together with chromium. When using such a catalyst, it is preferred to choose one in which the atomic percentage of zinc, based on the sum of zinc and chromium, is at least 60% and in particular 60–80%. The catalyst mixture that is used in the process according to the invention may be a macromixture or a micromixture. In the first case the catalyst mixture consists of two kinds of macroparticles, of which one kind consists completely of catalyst X, and the other kind completely of catalyst Y. In the second case the catalyst mixture consists of one kind of macroparticles, each macroparticle being built up of a great number of microparticles of each of the catalysts X and Y. Catalyst mixtures in the form of micromixtures may be prepared, for instance, by thoroughly mixing a fine powder of catalyst X with a fine powder of catalyst Y and shaping the mixture into larger particles, for instance, by extruding or tabletting. In the process according to the invention it is preferred to use catalyst mixtures in the form of micromixtures. In view of the required activity of the catalyst mixtures, preferred mixtures are those containing per part by volume of catalyst Y, 1–5 parts by volume of catalyst X.

The crystalline gallium silicate that is present in the catalyst mixtures as catalyst Y, is defined, inter alia, with reference to the X-ray powder diffraction pattern, which should contain, inter alia, the reflections shown in Table A. The complete X-ray powder diffraction pattern of a typical example of a gallium silicate suitable for use according to the invention is shown in Table B. (Radiation: Cu-K; wavelength; 0.15418 nm).

TABLE B

| $2\theta$ | relative intensity (100. I/I0) | description |
| --- | --- | --- |
| 8.00 | 55 | DP |
| 8.90 | 36 | SP |
| 9.10 | 20 | SR |
| 11.95 | 7 | NL |
| 12.55 | 3 | NL |
| 13.25 | 4 | NL |
| 13.95 | 10 | NL |
| 14.75 | 9 | BD |
| 15.55 | 7 | BD |
| 15.95 | 9 | BD |
| 17.75 | 5 | BD |
| 19.35 | 6 | NL |
| 20.40 | 9 | NL |
| 20.90 | 10 | NL |
| 21.80 | 4 | NL |
| 22.25 | 8 | NL |
| 23.25 | 100$^x$ | SP |
| 23.95 | 45 | SP |
| 24.40 | 27 | SP |
| 25.90 | 11 | BD |
| 26.70 | 9 | BD |
| 27.50 | 4 | NL |
| 29.30 | 7 | NL |
| 29.90 | 11 | BD |
| 31.25 | 2 | NL |
| 32.75 | 4 | NL |
| 34.40 | 4 | NL |
| 36.05 | 5 | BD |
| 37.50 | 4 | BD |
| 45.30 | 9 | BD |

$^xI_o$ = intensity of the strongest separate reflection present in the pattern.

The letters used in Table B for describing the reflections have the following meanings: SP=sharp; SR=shoulder; NL=normal; BD=broad; $\theta$=angle according to Bragg.

The crystalline gallium silicates which are used in the catalyst mixtures can be prepared from an aqueous starting mixture containing the following compounds:
one or more compounds of an alkali metal and/or alkaline-earth metal (M),
one or more compounds containing an organic cation (R) or from which such a cation is formed during the preparation of the silicate,
one or more silicon compounds and
one or more gallium compounds.

The preparation takes place by maintaining the mixture at elevated temperature until the silicate has been formed and subsequently separating the crystals of the silicate from the mother liquor and washing, drying and calcining the crystals. In the aqueous mixture from which the silicates are prepared, the various compounds should be present in the following ratios, expressed in moles of the oxides:

$(M)_{2/n}O:R_2O = 0.1-20$ $R_2O:SiO_2 = 0.01-0.5$ $SiO_2:Ga_2O_3 > 10$, and $H_2O:SiO_2 = 5-50$; n is the valency of M.

In the preparation of the silicates it is preferred to start from a base mixture in which M is present in a sodium compound and R in a tetrapropylammonium compound.

For the gallium silicates which are suitable for use in the process according to the invention the value of m should be lower than 0.1. Preference is given to the use of gallium silicates for which m is at least 0.0015 and particularly at least 0.002.

Although the crystalline silicates that are used in the process according to the invention are designated gallium silicates, they may contain in addition to gallium, a small amount of aluminum. The silicon compounds which are eligible for the preparation of crystalline silicates on a technical scale from an economical point of view, contain as a rule a small amount of aluminum as contaminant. As a rule, this aluminum is found, at least partly, in the silicate prepared.

The silicates prepared in the above-described way contain alkali metal ions and/or alkaline-earth metal ions. By using suitable exchange methods these ions can be replaced by other cations, such as hydrogen ions or ammonium ions. The crystalline gallium silicates which are used in the catalyst mixtures preferably have an alkali metal content of less than 0.1% w and particularly less than 0.05% w. If desired, a binder material such as bentonite or kaolin may be incorporated into the catalyst mixtures.

The process according to the invention can very suitably be carried out by conducting the feed in upward or downward direction through a vertically mounted reactor, in which a fixed or a moving bed of the catalyst mixture concerned is present. The process may, for instance, be carried out by conducting a feed in upward direction through a vertically mounted catalyst bed, using such a gas rate that expansion of the catalyst bed occurs. If desired, the process can also be carried out using a suspension of the catalyst mixture in a hydrocarbon oil. Depending on whether the process is carried out with a fixed catalyst bed, an expanded catalyst bed or a catalyst suspension, preference is given to catalyst particles with a diameter between 1 and 5 mm, 0.5 and 2.5 mm and 20 and 150 μm, respectively.

The invention will now be explained with reference to the following sample.

EXAMPLE

Nine crystalline silicates (silicates 1-9) were prepared by heating mixtures of $SiO_2$, NaOH, $[(C_3H_7)_4N]OH$ and either $NaAlO_2$, or $Ga(NO_3)_3$ for 24 hours in water in an autoclave at 150° C. under autogenous pressure. After the reaction mixtures had cooled down, the silicates formed were filtered off, washed with water until the pH of the wash water was about 8, dried at 120° C. and calcined at 500° C. Silicates 1-9 had the following properties:

(a) thermally stable up to a temperature above 800° C.,
(b) an X-ray powder diffraction pattern, substantially equal to the one given in Table B,
(c) a value for m as given in Table C.

TABLE C

| Silicate no. | $Ga_2O_3/SiO_2$ | $Al_2O_3/SiO_2$ |
|---|---|---|
| 1 | 0.0185 | — |
| 2 | 0.0179 | — |
| 3 | 0.0083 | — |
| 4 | 0.0058 | — |
| 5 | 0.0046 | — |
| 6 | 0.0026 | — |
| 7 | — | 0.0196 |
| 8 | — | 0.0064 |
| 9 | — | 0.0022 |

The molar composition of the aqueous mixtures from which silicates 1-9 were prepared can be represented as follows:

x $Na_2O.4.5[(C_3H_7)_4N]_2O$.y $Ga_2O_3$.z $Al_2O_3.25$ $SiO_2.450 H_2O$ wherein x, y, and z have the values given in Table D.

TABLE D

| Silicate No. | x | y | z |
|---|---|---|---|
| 1 | 1 | 0.33 | — |
| 2 | 3 | 0.33 | — |
| 3 | 1 | 0.22 | — |
| 4 | 1 | 0.125 | — |
| 5 | 1 | 0.063 | — |
| 6 | 1 | 0.043 | — |
| 7 | 1 | — | 0.33 |
| 8 | 1 | — | 0.125 |
| 9 | 1 | — | 0.042 |

Silicates 10-18 were prepared from silicates 1-9, respectively, by boiling silicates 1-9 with 1.0 molar $NH_4NO_3$ solution and washing, drying at 120° C. and calcining at 500° C. Subsequently, nine catalyst mixtures (catalyst mixtures A-I) were prepared by mixing a $ZnO-Cr_2O_3$ composition with each of the silicates 10-18. The atomic Zn percentage of the $ZnO-Cr_2O_3$ composition was 70%. The catalyst mixtures all contained per part by weight silicate 10 parts by weight of the $ZnO-Cr_2O_3$ composition. Catalyst mixtures A-I were tested for the preparation of an aromatic hydrocarbon mixture from an $H_2/CO$ mixture. The test was carried out in a 50-ml reactor containing a fixed catalyst bed having a volume of 7.5 ml. In nine experiments an $H_2/CO$ mixture with an $H_2/CO$ molar ratio of 0.5 was conducted over each of the catalyst mixtures A-I at a temperature of 375° C., a pressure of 60 bar and a space velocity of 1000 Nl. $l^{-1}.h^{-1}$. In all cases a product was obtained of which the $C_5^+$ fraction consisted of more than 50% aromatics. The other results of the experiments are listed in Table E.

TABLE E

| Exp. No. | Cat. mixture No. | Silicate No. | Conversion of synthesis gas after 10h, % | $C_5^+$ selectivity % w on $C_1^+$ |
|---|---|---|---|---|
| 1 | A | 10 | 67 | 77 |
| 2 | B | 11 | 68 | 75 |
| 3 | C | 12 | 67 | 72 |
| 4 | D | 13 | 67 | 78 |
| 5 | E | 14 | 67 | 78 |
| 6 | F | 15 | 66 | 78 |
| 7 | G | 16 | 66 | 50 |
| 8 | H | 17 | 60 | 58 |
| 9 | I | 18 | 41 | 70 |

Of the experiments listed in Table E only experiments 1-6, in which a catalyst mixture was used containing a crystalline gallium silicate, are experiments according to the invention. Experiments 7-9, in which a catalyst mixture was used containing a crystalline aluminum silicate, are outside the scope of the invention. They have been included for comparison.

The results listed in Table E show that in the conversion of an $H_2/CO$ mixture into an aromatic hydrocarbon mixture, using a catalyst mixture which contains a crystalline aluminum silicate, both the activity and the selectivity of the catalyst mixture are greatly dependent on m of the silicate incorporated in it. The results show further, that, if in the catalyst mixture the aluminum silicate is replaced by a gallium silicate, catalyst mixtures are obtained whose activity and selectivity for the conversion mentioned are independent of m of the silicate incorporated in it. Such higher activity and selectivity can result in significant economic advantages for commercialization of the process.

We claim as our invention:

1. A process for the preparation of an aromatic hydrocarbon mixture from a feed mixture of carbon monoxide and hydrogen wherein the molar ratio of hydrogen to carbon monoxide in the feed lies between 0.25 and 1.0 which comprises contacting said feed in a contacting zone at a temperature of 200°-500° C., a pressure of 1-150 bar and a space velocity of 50-5000 Nl gas/l catalyst/h with a mixture of two catalysts, a catalyst X containing zinc together with chromium and having the capability of catalyzing the conversion of an $H_2/CO$ mixture into acyclic oxygen-containing hydrocarbons and a catalyst Y being a crystalline gallium silicate, having the following properties:

(a) thermally stable up to a temperature above 600° C.,
(b) an X-ray powder diffraction pattern showing, inter alia, the reflections given in Table A of the specification,
(c) in the formula which gives the composition of the silicate, expressed in moles of the oxides, and in which, in addition to oxides of hydrogen, alkali metal and/or alkaline-earth metal and silicon, gallium oxide is present, the $Ga_2O_3/SiO_2$ molar ratio (m) is less than 0.1 to produce a contact product, and separating an aromatic hydrocarbon mixture from said contact product.

2. A process according to claim 1, wherein said contacting is carried out at a temperature of 300°-450° C., a pressure of 5-100 bar and a space velocity of 300-3000 Nl gas/l catalyst/h.

3. A process according to claim 1, wherein said catalyst X has the capability of converting an $H_2/CO$ mixture into substantially methanol and/or dimethyl ether.

4. A process according to claim 3, wherein in the catalyst X the atomic percentage of zinc, based on the sum of zinc and chromium, is at least 60%.

5. A process according to claim 4, wherein in the catalyst X the atomic percentage of zinc, based on the sum of zinc and chromium, is 60-80%.

6. A process according to claim 3, wherein the catalyst mixture contains per part by volume of catalyst Y 1-5 parts by volume of catalyst X.

7. A process according to claim 1, wherein the catalyst mixture contains a crystalline gallium silicate whose m is at least 0.0015.

8. A process according to claim 7, wherein m is at least 0.0020.

9. A process according to claim 1, wherein the catalyst mixture contains a crystalline silicate with an alkali metal content of less than 0.05% w.

* * * * *